US007026303B2

(12) United States Patent
Cimiluca et al.

(10) Patent No.: US 7,026,303 B2
(45) Date of Patent: Apr. 11, 2006

(54) COMPOSITIONS COMPRISING A POLYSACCHARIDE COMPONENT AND ONE OR MORE COATING LAYERS

(75) Inventors: Paul Alfred Cimiluca, Cincinnati, OH (US); Graham John Myatt, Camberley (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/633,965

(22) Filed: Aug. 4, 2003

(65) Prior Publication Data

US 2004/0162267 A1    Aug. 19, 2004

Related U.S. Application Data

(63) Continuation-in-part of application No. 10/368,510, filed on Feb. 18, 2003, now abandoned, and a continuation-in-part of application No. 10/368,514, filed on Feb. 18, 2003, and a continuation-in-part of application No. 10/369,039, filed on Feb. 18, 2003.

(51) Int. Cl.
*A61K 31/715* (2006.01)
*A01N 25/00* (2006.01)

(52) U.S. Cl. .................. 514/54; 514/884; 514/892
(58) Field of Classification Search .................. 514/54, 514/884, 892
See application file for complete search history.

(56) References Cited

U.S. PATENT DOCUMENTS

| 4,321,263 | A | | 3/1982 | Powell et al. |
| 4,548,806 | A | | 10/1985 | Colliopoulos et al. |
| 4,999,200 | A | | 3/1991 | Casillan |
| 5,009,916 | A | * | 4/1991 | Colliopoulos ............... 426/615 |
| 5,219,570 | A | | 6/1993 | Barbera |
| 5,320,847 | A | | 6/1994 | Valentine et al. |
| 5,356,618 | A | | 10/1994 | Daggy et al. |
| 5,425,945 | A | | 6/1995 | Barbera |
| 6,045,847 | A | * | 4/2000 | Nakamura et al. .......... 426/508 |
| 6,287,609 | B1 | | 9/2001 | Marlett et al. |

FOREIGN PATENT DOCUMENTS

| WO | WO 97/06808 A1 | 2/1997 |
| WO | WO 03/099311 A1 | 12/2003 |

\* cited by examiner

*Primary Examiner*—James O. Wilson
*Assistant Examiner*—Everett White
(74) *Attorney, Agent, or Firm*—Cynthia L. Clay; Kelly L. McDow-Dunham; Karen F. Clark

(57) ABSTRACT

The present disclosure provides compositions comprising a plurality of agglomerates comprising a polysaccharide component comprising xylose and arabinose, wherein the ratio of xylose to arabinose is at least about 3:1, by weight; wherein the compositions further comprise:
  (i) optionally, a first surrounding layer which surrounds the agglomerate, wherein the first surrounding layer is a hydrophobic layer; and
  (ii) optionally, a second surrounding layer which surrounds the agglomerate, wherein the second surrounding layer is a hydrophilic layer;
wherein the compositions comprise at least one of the first surrounding layer and the second surrounding layer, and wherein when the agglomerate comprises the first surrounding layer and the second surrounding layer then the first surrounding layer is a preceding layer relative to the second surrounding layer.

In another embodiment, the disclosure provides compositions comprising a plurality of polysaccharide particles, wherein the polysaccharide particles comprise a polysaccharide component comprising xylose and arabinose, wherein the ratio of the xylose to the arabinose is at least about 3:1, by weight, and wherein the polysaccharide particles have a mean particle size distribution of from about 0.001 microns to about 150 microns, wherein the polysaccharide particles each, independently, comprise:
  (i) optionally, a first surrounding layer which surrounds the particle, wherein the first surrounding layer is a hydrophobic layer; and
  (ii) optionally, a second surrounding layer which surrounds the particle, wherein the second surrounding layer is a hydrophilic layer;
wherein the polysaccharide particles each, independently, comprise at least one of the first surrounding layer and the second surrounding layer, and wherein when the particle comprises the first surrounding layer and the second surrounding layer then the first surrounding layer is a preceding layer relative to the second surrounding layer.

The present compositions are useful for the treatment of a variety of benefits, including providing treatment for gastrointestinal conditions or providing other gastrointestinal benefits.

44 Claims, No Drawings

COMPOSITIONS COMPRISING A POLYSACCHARIDE COMPONENT AND ONE OR MORE COATING LAYERS

CROSS REFERENCE TO RELATED APPLICATION

The present application is a continuation-in-part and claims priority under Title 35, United States Code § 120 to the following: U.S. application Ser. No. 10/368510, now abandoned, Ser. Nos. 10/368514, and 10/369039, all filed Feb. 18, 2003.

FIELD OF THE INVENTION

The present invention relates to compositions useful for the treatment of gastrointestinal conditions. In particular, the present invention relates to compositions comprising a defined polysaccharide component, wherein the composition is specifically formulated with one or more coating layers to allow ease of admixture with aqueous liquids to allow consumer acceptable oral administration. The compositions are useful for a variety of treatments including, for example, normalizing bowel function, inducing laxation, reducing serum cholesterol levels, and treatment of other gastrointestinal disorders and are formulated for easy and pleasurable oral consumption.

BACKGROUND OF THE INVENTION

Products containing psyllium seed husk are widely used for normalizing bowel function and incuding laxation. It has also been shown that psyllium seed husk is effective for reducing human serum cholesterol levels and in controlling blood glucose levels in diabetics. These benefits are typically achieved by ingestion of psyllium seed husk, which is obtained from the seed coat from plants of the genus *Plantago*. To render a laxative effect, a typical dose of psyllium seed husk in humans is from about 2.5 grams to about 20 grams, taken from about 1 to about 3 times per day. In order to administer such a large amount of psyllium seed husk, the husk is often milled or ground and subsequently dispersed in water or an aqueous beverage for consumption by the user (for example, METAMUCIL®, sold by The Procter & Gamble Company). In addition to milling, typically, sanitization of the psyllium seed husk is performed prior to any further processing, in order to reduce microbial contamination of the psyllium seed husk. This sanitation step can be costly and difficult to perform.

Psyllium seed husk contains natural mucilage, forming a gelatinous mass on contact with water. As a result, milled psyllium seed husk, with its increased surface area, exhibits very poor disperability and mixability in water as the particles can tend to agglomerate. Hydration takes place over the surface of the agglomerated aggregates to form gel-coated lumps, the interiors of which are still substantially dry. These lumps are extremely difficult to disperse. Various methods have been employed to improve the dispersability of milled psyllium husk in an aqueous medium. For example, U.S. Pat. No. 5,425,945 discloses a drink mix composition comprising agglomerated psyllium seed husk with an edible acid uniformly dispersed throughout the agglomerating coating to obtain improved mixability and dispersability.

However, once dispersed in an aqueous solution, the agglomerated psyllium husk quickly hydrates and gels with an accompanying increase in the viscosity of the drink solution. Again, various methods have been employed to reduce this gelation rate and provide an aesthetically pleasing product. U.S. Pat. No. 5,356,618 teaches that the addition of calcium citrate malate to a composition comprising milled psyllium seed husk results in a reduced gelation rate of the husk when mixed with an aqueous solution. However, despite these improvements, the consumer typically drinks the liquid in a relatively short period of time (less than about two minutes) in order to avoid having to drink an aesthetically unpleasant, high viscosity liquid.

Sanitized, milled psyllium seed husk has been incorporated in baked products, such as cookies, crackers and similar food items to render solid dosage forms. However, the rapid gelation of the psyllium seed husk can be noticeable in these preparations as well. Baked products containing such psyllium seed husk have a tendency to begin to gel in the mouth during consumption, resulting in an unpleasant mouthfeel and poor aesthetics. It is generally necessary to consume such baked products with significant amounts of water or aqueous liquid for ease of swallowing. In addition, such solid psyllium seed husk preparations must be large in size or, alternatively, multiple preparations must be consumed in order to deliver an effective amount of psyllium seed husk. Therefore, a psyllium containing composition that is convenient, easily administered and has improved aesthetics mouthfeel is still needed.

Other forms of products containing psyllium include swallowable tablets with acceptable dissolution properties, thus avoiding problems of poor mouthfeel. U.S. Pat. No. 4,999,200 teaches a swallowable tablet comprising psyllium, a binder, a wetting agent and a disintegrating agent. Unfortunately, swallowable psyllium tablets, while convenient, often have poor dissolution properties. Like the powdered drink mix, once introduced into an aqueous environment hydration takes place over the surface of the pill, creating a gel coating, while the interiors of the pill remain substantially dry. For swallowable pills this can lead to incomplete dissolution in the gastrointestinal tract.

Methods of fractionating psyllium seed husk into various polysaccharide fractions are known. Certain of the fractions of psyllium seed husk deliver the same therapeutic benefits as psyllium seed husk. For example, U.S. Pat. No. 6,287,609 teaches a multiple extraction process for obtaining three distinct fractions from psyllium husk, including an alkali soluble/acid gel-forming fraction, an alkali insoluble fraction, and an acid soluble fraction. The alkali soluble/acid gel-forming fraction has a slower rate of gelation than non-fractionated psyllium seed husk. However, appropriate formulation of such fractions in a consumer-acceptable product has still presented challenges.

After significant work toward consumer-acceptable products that contain certain fractions of psyllium seed husk, the present inventors have discovered that the inclusion of certain defined components are useful for such purpose, particularly in compositions which are intended for dilution in an aqueous liquid prior to consumption. In particular, it has been surprisingly discovered that compositions containing a defined ratio of xylose and arabinose, containing particles or agglomerates coated with specifically defined coating layers as described herein, provide excellent mouthfeel when dispersed in an aqueous liquid, excellent dispersion in such aqueous liquid, and decreased sedimentation over time in such aqueous liquid as compared to psyllium seed husk. In one embodiment of the invention, the inventors have discovered agglomerates containing the xylose and arabinose, which are coated with these described coating layers. In another embodiment, the inventors have discovered other compositions, optionally comprising agglomerates and components which are physically distinct from the agglomerates, wherein the particles of polysaccharide are coated with these described coating layers. These and other embodiments and benefits of the present invention are defined herein below.

SUMMARY OF THE INVENTION

In one embodiment, the present invention relates to compositions comprising a plurality of agglomerates comprising a polysaccharide component comprising xylose and arabinose, wherein the ratio of xylose to arabinose is at least about 3:1, by weight; wherein the composition further comprises:
  (i) optionally, a first surrounding layer which surrounds the agglomerates, wherein the first surrounding layer is a hydrophobic layer; and
  (ii) optionally, a second surrounding layer which surrounds the agglomerates, wherein the second surrounding layer is a hydrophilic layer;

wherein the composition comprises at least one of the first surrounding layer and the second surrounding layer, and wherein when the composition comprises the first surrounding layer and the second surrounding layer then the first surrounding layer is a preceding layer relative to the second surrounding layer.

In another embodiment, the invention relates to compositions comprising a plurality of polysaccharide particles, wherein the polysaccharide particles comprise a polysaccharide component comprising xylose and arabinose, wherein the ratio of the xylose to the arabinose is at least about 3:1, by weight, and wherein the polysaccharide particles have a mean particle size distribution of from about 0.001 microns to about 150 microns, wherein the polysaccharide particles each, independently, comprise:
  (i) optionally, a first surrounding layer which surrounds the particle, wherein the first surrounding layer is a hydrophobic layer; and
  (ii) optionally, a second surrounding layer which surrounds the particle, wherein the second surrounding layer is a hydrophilic layer;

wherein the polysaccharide particles each, independently, comprise at least one of the first surrounding layer and the second surrounding layer, and wherein when the particle comprises the first surrounding layer and the second surrounding layer then the first surrounding layer is a preceding layer relative to the second surrounding layer.

The present compositions are useful for the treatment of a variety of benefits, including providing treatment for gastrointestinal conditions or providing other gastrointestinal benefits. Methods of providing a benefit selected from normalizing bowel function, inducing laxation, providing dietary fiber, reducing serum cholesterol levels, and combinations thereof are described herein, wherein the methods comprise:
  (a) admixing a foregoing composition with an aqueous liquid to form a product; and
  (b) orally administering the product.

DETAILED DESCRIPTION OF THE INVENTION

Various documents including, for example, publications and patents, are recited throughout this disclosure. All such documents are hereby incorporated by reference.

All percentages and ratios are calculated by weight unless otherwise indicated. All percentages and ratios are calculated based on the total composition unless otherwise indicated.

Referenced herein are trade names for components including various ingredients utilized in the present invention. The inventors herein do not intend to be limited by materials under a certain trade name. Equivalent materials (e.g., those obtained from a different source under a different name or reference number) to those referenced by trade name may be substituted and utilized in the descriptions herein.

In the description of the invention various embodiments and/or individual features are disclosed. As will be apparent to the ordinarily skilled practitioner, all combinations of such embodiments and features are possible and can result in preferred executions of the present invention.

The compositions herein may comprise, consist essentially of, or consist of any of the elements as described herein.

While various embodiments and individual features of the present invention have been illustrated and described, various other changes and modifications can be made without departing from the spirit and scope of the invention. As will also be apparent, all combinations of the embodiments and features taught in the foregoing disclosure are possible and can result in preferred executions of the invention.

The Compositions of the Present Invention

The present invention relates to compositions comprising a polysaccharide component, wherein the compositions contain either agglomerates or polysaccharide particles which are coated in a specified manner. In particular, the present invention is directed to either of two key embodiments. In the first embodiment, the invention relates to compositions comprising a plurality of agglomerates comprising a polysaccharide component comprising xylose and arabinose, wherein the ratio of xylose to arabinose is at least about 3:1, by weight; wherein the composition further comprises:
  (i) optionally, a first surrounding layer which surrounds the agglomerates, wherein the first surrounding layer is a hydrophobic layer; and
  (ii) optionally, a second surrounding layer which surrounds the agglomerates, wherein the second surrounding layer is a hydrophilic layer;

wherein the composition comprises at least one of the first surrounding layer and the second surrounding layer, and wherein when the composition comprises the first surrounding layer and the second surrounding layer then the first surrounding layer is a preceding layer relative to the second surrounding layer.

The present invention may optionally comprise from about 10% to about 90% of polysaccharide component, or from about 20% to about 40% of polysaccharide component, or from about 20% to about 50% polysaccharide component, or from about 20% to about 60% polysaccharide component, or from about 20% to about 70% polysaccharide component, or from about 20% to about 80% polysaccharide component, or from about 30% to about 70% polysaccharide component. In another preferred embodiment in accordance with the discoveries herein, the agglomerates comprise various further defined levels of polysaccharide component.

In another embodiment, the invention relates to compositions comprising a plurality of polysaccharide particles, wherein the polysaccharide particles comprise a polysaccharide component comprising xylose and arabinose, wherein the ratio of the xylose to the arabinose is at least about 3:1, by weight, and wherein the polysaccharide particles have a mean particle size distribution of from about 0.001 microns to about 150 microns, wherein the polysaccharide particles each, independently, comprise:

(i) optionally, a first surrounding layer which surrounds the particle, wherein the first surrounding layer is a hydrophobic layer; and (ii) optionally, a second surrounding layer which surrounds the particle, wherein the second surrounding layer is a hydrophilic layer;

wherein the polysaccharide particles each, independently, comprise at least one of the first surrounding layer and the second surrounding layer, and wherein when the particle comprises the first surrounding layer and the second surrounding layer then the first surrounding layer is a preceding layer relative to the second surrounding layer.

The various components of the compositions, including preferred embodiments and optional components, are described herein as follows:

The Polysaccharide Component

The agglomerates or polysaccharide particles, as applicable, comprises a polysaccharide component, wherein the polysaccharide component comprises xylose and arabinose, wherein the ratio of xylose to arabinose is at least about 3:1, by weight. In alternative embodiments, the present compositions comprise xylose and arabinose, wherein the ratio of xylose to arabinose is at least about 3.3:1, or at least about 3.6:1, all by weight. In other embodiments, the present compositions comprise xylose and arabinose, wherein the ratio of xylose to arabinose is from about 3:1 to about 4.5:1, or from about 3:1 to about 4:1, all by weight.

The polysaccharide component optionally comprises from about 55% to about 70% xylose, by weight of the polysaccharide component. The polysaccharide component may also optionally comprise from about 15% to about 20% arabinose, by weight of the polysaccharide component.

The polysaccharide component may also optionally comprise a component selected from the group consisting of galactose, glucose, uronic acid, and mixtures thereof. These components may be present in low amounts relative to the xylose and arabinose.

For example, the polysaccharide component may optionally comprise less than about 2%, or from about 1% to about 2%, of galactose, all by weight of the polysaccharide component.

As another example, the polysaccharide component may optionally comprise less than about 2%, or from about 0.01% to about 1% of glucose, all by weight of the polysaccharide component.

As another example, the polysaccharide component may optionally comprise less than about 20%, or from about 1% to about 10%, or from about 0.1% to about 5% of uronic acid, all by weight of the polysaccharide component.

In another embodiment herein, the polysaccharide component comprises xylose and galactose, wherein the ratio of xylose to galactose is greater than about 25:1, or greater than about 30:1, or greater than about 35:1, all by weight.

In another embodiment herein, the polysaccharide component comprises xylose and uronic acid, wherein the ratio of xylose to uronic acid is greater than about 5:1, or greater than about 10:1, or greater than about 15:1, all by weight.

The polysaccharide component may optionally further comprise a component selected from rhamnose, mannose, and mixtures thereof.

Other preferred embodiments include those polysaccharide components comprising one or both, or a portion of, Fraction B or C as described in U.S. Pat. No. 6,287,609.

In one embodiment of the invention, the composition comprises a plurality of polysaccharide particles, wherein the polysaccharide particles comprise the polysaccharide component and wherein the polysaccharide particles have a mean particle size distribution of from about 0.001 microns to about 150 microns. In another embodiment, the polysaccharide particles have a mean particle size distribution of from about 0.1 microns to about 125 microns, or from about 1 micron to about 100 microns.

In this embodiment of the invention, the composition comprises the polysaccharide particles, wherein the polysaccharide particles optionally have the defined mean particle size distribution. The polysaccharide particles may be freely dispersed throughout the composition or may be agglomerated with other components which are compositionally distinct, to form an agglomerate. Thus, the polysaccharide particles may have one mean particle size distribution and may optionally be agglomerated to form agglomerates having another mean particle size distribution, as described herein below with respect to the agglomerates.

Optional Dispersing Component

In an optional embodiment herein, the composition may further comprise a dispersing component selected from binders, suspending agents, edible acids, and mixtures thereof. After significant work toward more consumer-acceptable products, the present inventors have discovered that the inclusion of these certain defined components are useful for such purpose, particularly in compositions which are intended for dilution in an aqueous liquid prior to consumption. In particular, the present inventors have discovered that inclusion of the dispersing component as defined herein provides excellent properties in terms of dispersion or dissolution, mouthfeel, or resistance to sedimentation upon admixture with an aqueous liquid. The discovery of these properties has led to products that will be more acceptable to the consumer relative to previous compositions containing psyllium seed husk.

In one embodiment, the dispersing component may optionally be freely dispersed throughout the composition. In another embodiment, the dispersing component may be agglomerated with other components which are compositionally distinct, to form an agglomerate. In yet another embodiment, the compositions comprise the dispersing component wherein at least a portion of the dispersing component is physically distinct from the agglomerates.

As stated, the dispersing component is selected from binders, suspending agents, edible acids, and mixtures thereof. Each of these components will be well-known to the ordinarily skilled artisan, however, examples are provided herein below.

Binders are known in the art. Examples of useful binders for the purposes herein are found to be polyols, starches, gums, or mixtures thereof. Polyols and starches are particularly preferred for use herein.

Polyols include sugar alcohols such as disaccharides and complex carbohydrates. Certain complex carbohydrates are referred commonly as starches. Disaccharides are molecules having the general formula $C_nH_{2n-2}O_{n-1}$, wherein the disaccharide has 2 monosaccharide units connected via a glycosidic bond. In such formula, n is an integer equal to or greater than 3. Examples of disaccharides which may be utilized herein include sucrose, maltose, lactitol, maltitol, maltulose, and lactose.

Complex carbohydrates include oligosaccharides and polysaccharides. As used herein, the term "oligosaccharide" means a molecule having from 3 to 9 monosaccharide units, wherein the units are covalently connected via glycosidic bonds. As used herein, the term "polysaccharide" means a macromolecule having greater than 9 monosaccharide units, wherein the units are covalently connected via glycosidic bonds. The polysaccharides may be linear chains or branched. Preferably, the polysaccharide has from 9 to about 20 monosaccharide units. Polysaccharides may include starches, which is defined herein to include starches and modified starches. Starches are generally carbohydrate polymers occurring in certain plant species, for example, cereals and tubers, such as corn, wheat, rice, tapioca, potato, pea, and the like. Starches contain linked alpha-D-glucose units. Starches may have either a mainly linear structure (e.g., amylose) or a branched structure (e.g., amylopectin). Starches may be modified by cross-linking to prevent excessive swelling of the starch granules using methods well-known to those skilled in the art.

Examples of preferred complex carbohydrates include raffinose, stachyoses, maltotriose, maltotetraose, glycogen, amylose, amylopectin, polydextrose, and maltodextrin. The most preferred complex carbohydrate, and indeed the most preferred binder, is maltodextrin. Other examples of starches include potato starch, corn starch, and the like. Other examples of commercially available starches include ULTRA SPERSE M, ULTRA-SPERSE 2000, N-LITE LP, and TEXTRA PLUS, all available from National Starch and Chemical Company, Bridgewater, N.J.

The present compositions may optionally comprise from about 1% to about 50% of the binder, by weight of the composition. In another embodiment, the compositions comprise from about 10% to about 40%, alternatively from about 20% to about 30% of the binder, all by weight of the composition.

Suspending agents are also well-known in the art. Gums, including other hydrocolloids, may also be utilized as the suspending agent. As used herein, the term "hydrocolloid gums" or simply "gums" refers to plant or microbial polysaccharides or their derivatives that are dispersible in either cold or hot water to produce viscous mixtures or solutions. Examples of gums include tara gum, gellan gum, guar gum, xanthan gum, gum arabic, gum ghatti, tragacanth gum, locust bean gum, carboxymethylcellulose, alginates, and the like. Particularly preferred gums include tara gum and guar gum.

The present compositions may optionally comprise from about 0.001% to about 20% of the suspending agent, by weight of the composition. In another embodiment, the compositions comprise from about 0.1% to about 10%, alternatively from about 0.5% to about 5% of the suspending agent, alternatively from about 1% to about 3% of the suspending agent, all by weight of the composition.

In addition to, or alternative to, the binder or suspending agent is the edible acid. It has been found herein that inclusion of an edible acid assists with a decrease in the rate of gellation of the polysaccharide component herein when such component is admixed with an aqueous liquid. Edible acids are commonly known in the art and include acids that are safe for oral administration in mammals. Examples of edible acids include lactic acid, citric acid, malic acid, fumaric acid, adipic acid, phosphoric acid, gluconic acid, tartaric acid, ascorbic acid, acetic acid, phosphoric acid, succinic acid, and mixtures thereof. In one embodiment, the edible acid source is selected from citric acid, malic acid, tartartic acid, fumaric acid, succinic acid, and mixtures thereof. In another embodiment, the edible acid source is citric acid.

The present compositions typically comprise relatively low levels of the edible acid. For example, the compositions may comprise less than about 10% of edible acid, by weight of the composition. In another embodiment the compositions comprise from 0% to about 8%, or from about 0.001% to about 5%, or from about 0.01% to about 3% of the edible acid, all by weight of the composition.

The Agglomerate

The inventors have further discovered herein that the use of agglomerates comprising at least a portion of the polysaccharide component, and optionally the dispersing component or other components, may result in even further benefits in terms of dispersion or dissolution, mouthfeel, or resistance to sedimentation. As part of this discovery, compositions comprising such agglomerates are preferred embodiments of this invention.

It has been found that the most preferred, optimal, agglomerates have a particle size of from about 100 microns to about 500 microns. As such, preferred among the compositions herein comprise agglomerates having a mean particle size distribution of from about 100 microns to about 400 microns, or from about 125 microns to about 350 microns, or from about 150 microns to about 320 microns. As used herein, and as will be commonly understood in the art, the term "mean particle size distribution," with reference to the agglomerate, is the mean value of the agglomerate particles present in the composition based on the particle sizes of the individual agglomerate particles in the composition. The mean particle size distribution of the agglomerates may be measured using a HORIBA LA-910 laser scattering particle size distribution analyzer (Horiba, Calif.), or other instrument providing substantially similar results.

Various levels of polysaccharide component and dispersing component have already been described, and may also be referenced wherein the composition comprises the agglomerates. In another preferred embodiment in accordance with the discoveries herein, the agglomerates comprise various further defined levels of polysaccharide component or dispersing component. In one embodiment, the agglomerates comprise from about 10% to about 90% of xylose and arabinose, or from about 20% to about 80% of xylose and arabinose, or from about 30% to about 70% of xylose and arabinose, all by weight of the agglomerates. In another embodiment, the agglomerates comprise from about 10% to about 90% of binder, or from about 10% to about 60% of binder, or from about 20% to about 50% of binder, or from about 30% to about 40% of binder, all by weight of the agglomerates. In another embodiment, the agglomerates comprise from about 10% to about 90% of the suspending agent, or from about 10% to about 60% of suspending agent, or from about 20% to about 50% of suspending agent, or from about 30% to about 40% of suspending agent, all by weight of the agglomerates. In another embodiment, the agglomerates comprise from 0% to about 10% of edible acid, or from about 0.001% to about 8% of edible acid, or from about 1% to about 6% of edible acid, or from about 4% to about 6% of edible acid, all by weight of the agglomerates. As used herein, the various levels of ingredients referenced for the agglomerates is based on the total agglomerates present in the composition, rather than each individual agglomerate present in the composition. For example, wherein "the agglomerates comprise from about 10% to about 90% of xylose and arabinose, by weight of the agglomerates," this means that the total of all agglomerates present in the composition comprise from about 10% to about 90% of xylose and arabinose, by weight of the total agglomerates. Since the levels of various ingredient can vary from agglomerate-to-agglomerate, this is not intended to mean that each individual agglomerate must contain from about 10% to about 90% of xylose and arabinose, by weight of the individual agglomerate.

The Surrounding Layers

Pursuant to the present invention, the compositions comprise a plurality of agglomerates or polysaccharide particles which are coated with at least one or more surrounding layers (as has been described above). Using the agglomerate as an example, the agglomerate may be joined to one or more surrounding layers, which surround the polysaccharide particle. Using the polysaccharide particle as an example, the polysaccharide particle may be joined to one or more surrounding layers, which surround the polysaccharide particle. As used herein, the terms "joined to," or the like means surrounding the agglomerate, or polysaccharide particle, or the like, in such a manner that the layer is contiguous with either the agglomerate or polysaccharide component itself, a preceding layer, or a succeeding layer. The layer may be "joined to" the agglomerate or polysaccharide component, a preceding layer, or a succeeding layer even though other matter (such as another preceding or succeeding layer) intervenes. Accordingly, a layer which is "joined to" the agglomerate or polysaccharide component need not actually be contiguous with such agglomerate or polysaccharide component.

As used herein, the term "contiguous with" means directly joined by physical forces with essentially no intervening matter. For example, the first surrounding layer may be contiguous with the agglomerate (or polysaccharide component, as appropriate) as well as a succeeding layer (wherein the succeeding layer is either another layer or the second surrounding layer). As another example, the second surrounding layer may be contiguous with the agglomerate or another layer. Using the agglomerates as an example, wherein a given agglomerate comprises both the first surrounding layer and the second surrounding layer, the second surrounding layer is not contiguous with the agglomerate, because the first surrounding layer is a preceding layer relative to the second surrounding layer.

As used herein, the term "preceding layer" means a layer which is joined to the agglomerate or polysaccharide particle, as applicable, and is closer in proximity to such agglomerate or polysaccharide particle relative to a reference layer joined to the same agglomerate or polysaccharide particle. For example, wherein both are present, the first surrounding layer is a preceding layer relative to the second surrounding layer.

As used herein, the term "succeeding layer" means a layer which is joined to the agglomerate or polysaccharide particle, as applicable, but is further in proximity from the agglomerate or polysaccharide particle relative to a reference layer joined to the same agglomerate or polysaccharide particle. For example, wherein both are present, the second surrounding layer is a succeeding layer relative to the first surrounding layer.

Preferably, each layer is continuous. As used herein, the term "continuous" means that the referenced layer is not disrupted by a void at any point.

In one embodiment, the agglomerate or polysaccharide particle, as applicable, is joined to the first surrounding layer which is a hydrophobic layer, preferably a continuous hydrophobic layer. The hydrophobic layer therefore comprises one or more materials, such that the hydrophobic layer is hydrophobic. The present inventors have discovered that inclusion of an agglomerate comprising such a hydrophobic layer is particularly useful to inhibit the final agglomerate from absorbing water, thereby reducing the ability of the agglomerate to form an undesirable gel. These benefits are similarly achieved wherein the polysaccharide particle is coated with a surrounding layer which is a hydrophobic layer, preferably a continuous hydrophobic layer.

In a preferred, but optional, embodiment of the present invention, the term hydrophobic, with reference to the hydrophobic layer, means that the hydrophobic layer exhibits a water vapor transmission rate (WVTR) of less than about 200 mg/m$^2$/24 hours (defined herein as measured using the ISO International Standard entitled "Sheet Materials—Determination of Water Vapour Transmission Rate—Gravimetric (Dish) Method" (Reference Number ISO 2528: 1995(E)). In another embodiment, the term hydrophobic, with reference to the hydrophobic layer, means that the hydrophobic layer has a water vapor transmission rate (WVTR) of less than about 100 mg/m$^2$/24 hours using this Standard (again, defined herein as measured using the ISO International Standard entitled "Sheet Materials—Determination of Water Vapour Transmission Rate—Gravimetric (Dish) Method" (Reference Number ISO 2528:1995(E)).

Examples of preferred materials that may be included in the hydrophobic layer include fatty acids (e.g., stearic acid), fatty acid derivatives, polymers, and mixtures thereof. Most preferably, these materials are hydrophobic, such that the hydrophobic layer is made hydrophobic through inclusion of the material.

Fatty acid derivatives can include fats (e.g. fatty acid glyceryl esters, e.g., hydrogenated vegetable oils) and waxes (e.g., animal, fossil, vegetable, mineral, or synthetic waxes, such as carnuba, beeswax, carob, candelilla, ozocerite, polyethylene waxes, paraffin waxes, mixtures thereof, and the like). A wax is particularly preferred. Polymers can include polyvinylpyrrolidone, polymethacrylate, vinyl acetate, ethyl cellulose, cellulose acetate phthalate (e.g., AQUATERIC), cellulose acetate trimelliate, carboxymethyl ethyl cellulose, hydroxypropyl methyl cellulose acetate succinate, hydroxypropyl methyl cellulose phthalate, mixtures thereof, and the like. Most preferably, the outer layer comprises a material selected from the group consisting of fatty acids, fatty acid derivatives, and mixtures thereof.

In an optional embodiment herein the hydrophobic layer is a continuous coating having a coating weight of from about 3 mg/cm$^2$ to about 25 mg/cm$^2$, more preferably from about 4 mg/cm$^2$ to about 20 mg/cm$^2$. As used herein, coating weights are expressed in terms of mg/cm$^2$, referring to milligrams (mg) of referenced layer per square centimeter (cm$^2$) of referenced layer.

In another embodiment, particularly wherein the hydrophobic layer is utilized, it is found that a second surrounding layer which is a hydrophilic layer is additionally beneficial. Indeed, while the hydrophobic layer inhibits the absorption of water into the agglomerate or particle (as applicable), the hydrophilic layer is useful for further enhancing dispersion of the final agglomerate or particle in an aqueous liquid prior to administration.

Examples of preferred materials that may be included in the hydrophilic layer include surfactants (e.g., TWEENS, SPANS, and PLURONICS), gums (e.g., gum acacia), inorganic salts (e.g., calcium chloride, magnesium sulfate, calcium carbonate, calcium citrate, calcium phosphate, calcium chloride, calcium citrate-malate, magnesium carbonate, zinc acetate, and the like), and mixtures thereof. Most preferably, these materials are hydrophilic, such that the hydrophilic layer is made hydrophilic through inclusion of this material.

Wherein both a hydrophobic layer and a hydrophilic layer are utilized, the hydrophobic layer is preferably a preceding layer relative to the hydrophilic layer (i.e., the hydrophobic layer is more proximal to the agglomerate or polysaccharide particle (as applicable) relative to the hydrophilic layer). Most preferably, the hydrophilic layer is the outermost layer relative to the agglomerate or polysaccharide particle (as applicable).

Other Preferred Embodiments

As stated, the agglomerates may comprise the dispersing component in addition to the polysaccharide component. Wherein a given composition comprises such agglomerates, the composition may further comprise dispersing component which is admixed, but not agglomerated, with the agglomerates. Indeed, in a particularly preferred embodiment herein, the composition comprises the agglomerates as well as one or more further components, such as at least a portion of the dispersing component described above, wherein the agglomerates and at least a portion of the components are physically distinct. In this embodiment, the agglomerates and other components may be dry blended or otherwise admixed.

In a particularly preferred embodiment of this type, the compositions comprise a starch or gum, wherein at least a portion of such starch or gum is physically distinct from the agglomerates. In another embodiment, the compositions comprise a starch and a gum, wherein at least a portion of the starch and gum are physically distinct from the agglomerates. The inventors have discovered that this embodiment is particularly useful for reducing particulate sedimentation upon admixture with an aqueous liquid, thereby creating a more uniform product. Mouthfeel and overall texture may also be enhanced in accordance with this embodiment.

Preferred types of such components, as well as levels thereof present in the overall composition, have been described herein above with respect to the dispersing component.

Other Optional Components

One or more other optional components may be included in the compositions. For example, one or more cellulosic materials, emulsifiers or lubricating agents, flavorants, pigments, dyes, colorants and their corresponding lakes, nutrients, or sweeteners may be added to further enhance the compositions herein. Examples of such optional components follows:

One or more cellulosic materials are particularly useful for increasing the water solubility of the present compositions. Cellulosic materials are widely known in the art, as exemplified by AVICEL, methyl cellulose, and sodium carboxymethyl cellulose.

One or more emulsifiers, surfactants, or lubricating agents may be added to the compositions of the present invention. These may be particularly useful for increasing the water solubility of the present compositions. Examples include, but are not limited to, lecithin, talc, magnesium stearate, calcium stearate, stearic acid, hydrogenated vegetable oils, polyethylene glycol, sodium benzate, sodium chloride, leucine, sodium lauryl sulfate, and magnesium lauryl sulfate. Emulsifiers, surfactants, and lubricants are generally present, each independently, at a level of less than about 5%, by weight of the composition, and in one embodiment less than about 1%, by weight of the composition.

The compositions described herein may optionally further comprise one or more flavorants. Flavoring agents may optionally be chosen from synthetic flavoring liquids or oils derived from plants, leaves, flowers, fruits and the like, and mixtures thereof. Representative flavoring liquids include: vanillin, sage, marjoram, parsley oil, spearmint oil, cinnamon oil, oil of wintergreen (methylsalicylate), peppermint oils, clove oil, bay oil, anise oil, and eucalyptus oil. Also useful are artificial, natural or synthetic fruit flavors such as citrus oils, including lemon, orange, banana, grape, lime, apricot and grapefruit, and fruit essences, including apple, strawberry, cherry, orange, pineapple and so forth; bean and nut derived flavors such as coffee, cocoa, cola, peanut, almond; and spices such as cinnamon, nutmeg, ginger and the like. Flavors may optionally be encapsulated.

The amount of flavorant employed is normally a matter of preference subject to such factors as flavor type and strength of flavor desired. The flavorant may be incorporated into one or more of the following: the tablet; the coating of the tablet; or the coating of the individual particles of gel-forming polysaccharide, where such coatings are employed. Flavorants may be present in amounts up to about 4%, in one embodiment from about 0.01% to about 3%, in another embodiment from about 0.2% to about 2.5%, all by weight of the composition.

One or more pigments, dyes, colorants and their corresponding lakes may also be included to modify the appearance of the compositions herein to render the product more acceptable to the consumer. Appropriate levels are selected for the particular impact that is desirable to the consumer. The levels of pigments and colorants may optionally be in the range of from about 0.001% to about 20%, in one embodiment from about 0.01% to about 15% and in another embodiment from about 0.1% to about 10%, all by weight of the composition.

Examples of pigments and colorants include talc, mica, magnesium carbonate, calcium carbonate, magnesium silicate, aluminum magnesium silicate, silica, titanium dioxide, zinc oxide, red iron oxide, brown iron oxide, yellow iron oxide, black iron oxide, ferric ammonium ferrocyanide, bismuth oxychloride, manganese violet, ultramarine, nylon powder, polyethylene powder, methacrylate powder, polystyrene powder, silk powder, crystalline cellulose, starch, titanated mica, iron oxide titanated mica, bismuth oxychloride, FD&C Red 40, D&C Reds 3, 22, 28, 33 and 36, FD&C Yellows 5 and 6, D&C Yellow 10, FD&C Blues 1 and 2, FD&C Green 3, beta-carotene, caramel, cochineal extract, canthaxanthinin, and mixtures thereof.

One or more nutrients may be included in the compositions of the present invention. Nutrients include minerals, vitamins, oral nutritional supplements, enteral nutritional supplements, herbals and mixtures thereof. Useful minerals include calcium, phosphorus, zinc, manganese, potassium, sodium, chromium, cobalt, copper, fluorine, chlorine or chloride, iodine, iron, magnesium, molybdenum, selenium, silicon, boron, tin, vanadium and mixtures thereof. Vitamins can be included with minerals or used independently. Examples of vitamins include Vitamins A, C, $B_6$, $B_{12}$, D, E and K, thiamine, riboflavin, pantothenic acid, niacin, folic acid, nicotinamide, bioflavonoids, carnitine, coenzyme Q, biotin, and mixtures thereof. Examples of nutritional supplements include amino acids, lipotropics, fish oil, and mixtures thereof. Lipotropics include, but are not limited to, choline, inositol, betaine, linoleic acid, linolenic acid, and mixtures thereof. Fish oil contains large amounts of omega-3 (N-3)

polyunsaturated fatty acids, eicosapentaenoic acid and docosahexaenoic acid. Enteral nutritional supplements include, but are not limited to, protein products, glucose polymers, corn oil, safflower oil, medium chain triglycerides. Examples of herbals include, but are not limited to, wormwood (artemisia absinthium), mugwort (artemisiae herba), aniseed (anisi fructus), peppermint (menthae pipertiae folium), rosehips (rosae pseudofructus), and mixtures thereof. Herbals are described in more detail in *Herbal Drugs and Phytopharmaceuticals; A Handbook for Practice on a Scientific Basis*, CRC Press, Stuttgart, Germany, 1994.

The present compositions may further comprise one or more sweeteners, which may be additional to the polyols described herein above. Suitable sweeteners include natural and artificial, water soluble, water insoluble and intense sweeteners. The sweetening agent may be dextrose, sucrose, maltose, dextrin, dried invert sugar, mannose, xylose, ribose, glucose, fructose, levulose, galactose, corn syrup, high fructose corn syrup, corn syrup solids, partially hydrolyzed starch, aspartame, saccharin, and hydrogenated starch hydrolysate or combinations thereof. Natural or artificial intense sweeteners such as dipeptide based intense sweeteners, monellin, thaumaoccous danielli, and L-aspartyl L-phenylalanine methyl ester and soluble saccharin salts may also be incorporated as sweeteners. The amount of the sweetener will vary with the type of sweetener selected and the desired level of sweetness. Sweetening agents may optionally be used in the present compositions at levels of from about 0.005% to about 5%, by weight of the composition.

Methods of Making

The present compositions may be made in accordance with any of a variety of methods that will be well-known in the art. As an example, the polysaccharide component may be prepared as described in U.S. Pat. No. 6,287,609, or as follows:

Step 1. Suspending unmilled psyllium seed husk ("psyllium") in a dilute alkaline aqueous solution containing a reducing agent.

Step 2. Where previously unsanitized psyllium is utilized, disinfecting the alkali soluble and alkali insoluble material by any means known in the art such as pasteurization, irradiation, electron beam or pulsed light.

Step 3. Removing the alkali insoluble material by any process known in the art, for example centrifugation, filtration, expression or settling.

Step 4. Acidifying the solution to a pH of about 4.5 to about 6.5 by the addition of acid, to yield an acid gel-forming material, i.e., a gel-forming polysaccharide.

Step 5. Dewatering the acid gel-forming material by the addition of a desiccant with high shear mixing and then separating the gel material from the desiccant/water solution.

Step 6. Extruding the acid gel-forming material into individual particles with an average particle size of greater than 250 microns.

Step 7. Fluidized bed drying the acid gel-forming material rendering the compressible acid gel-forming material in powder form.

The starting material employed in the fractionation of psyllium seed husk may or may not be milled or physically altered or refined, prior to the initial alkaline solubilization step. U.S. Pat. No. 6,287,609 teaches that psyllium seed husk should be processed so that it is in small pieces, prior to alkaline solubilization, for ease of separation of the viscous polysaccharides from the insoluble fibers of the psyllium husk. However, clumping and agglomeration of the milled psyllium seed husk occurs when the milled husk is added to the alkaline mixture. Use of unmilled psyllium seed husk as an initial starting material avoids clumping or agglomerating of the psyllium material during mixing with the alkaline solution, but does not hinder the effectiveness of the alkaline solubilization step. The use of unmilled psyllium as a starting material for the fractionation provides a gel-forming polysaccharide with increased swell volume. The swell volume of the acid gel-forming material is greater than about 40 milliliters of gel per 0.5 grams dry gel-forming polysaccharide, in one embodiment greater than about 50 milliliters of gel per 0.5 grams dry gel-forming polysaccharide. The percent yield of the acid gel-forming material is at least about 75%, in one embodiment at least about 80%. The psyllium seed husk of the present invention may or may not be sanitized prior to processing. The psyllium seed husk may be sanitized or unsanitized prior to alkaline solubilization. Where raw (unsanitized) psyllium is used in the fractionation process, a disinfection step is incorporated in the fractionation process and may be carried out as described below.

Alkaline solubilization (Step 1) of psyllium seed husk is known. Typically, previous alkaline solubilization processes utilized concentrations of strong bases and lacked the presence of a reducing agent. Recognizing the harsh nature of this treatment and the partial degradation of polysaccharide chains in the gel-forming fraction, it has been shown that a gel-forming fraction of psyllium husk could be obtained, presumably in a form more suitable for further fractionation, if desired, using a much less concentrated alkaline solution and a suitable reducing agent, such as borohydride. Though up to about 4N alkaline solution can be utilized, the concentration of base in the alkaline solubilization is at least about 0.1N and not more than about 1.0N; in one embodiment at least about 0.1N and not more than about 0.5N; and in yet another embodiment at least about 0.1N and not more than about 0.3N. Any standard base can be used in the alkaline extraction, including, but not limited to, sodium hydroxide, potassium hydroxide, lithium hydroxide, ammonium hydroxide, and tetramethyl ammonium hydroxide. A suitable ratio of psyllium seed husks to alkaline solution is from about 0.1 gram seed husk to about 400 ml (milliliters) of alkaline solution to about 4 grams seed husk to about 400 ml alkaline solution. The alkaline solubilization should be carried out at a pH of from about 9 to about 12.

A chemical reducing agent, such as borohydride, should be added to the alkaline solubilization step to minimize base-catalyzed depolymerization. Borohydrides suitable for this step include, but are not limited to, lithium borohydride, potassium borohydride and sodium cyanoborohydride. In one embodiment the reducing agent is sodium borohydride. An effective concentration of a reducing agent is from about 50 mg/L (milligrams/liter) to about 10 g/L (grams/liter), in one embodiment from about 100 mg/L to about 4 g/L, in another embodiment from about 500 mg/L to about 2 g/L, and in yet another embodiment from about 800 mg/L to about 1.2 g/L.

The time of solubilization can be varied from about 15 minutes to about 24 hours, in one embodiment from about 30 minutes to about 180 minutes, for optimum efficiency. Likewise, the temperature at which the solubilization step is conducted can vary from about 5° C. to about 40° C. In one embodiment the time of solubilization is from about 60 minutes to about 120 minutes at ambient temperature. The alkaline solubilization may optionally be carried out in a nitrogen atmosphere to prevent oxidation from occurring.

The disinfecting step, Step 2, is required when the psyllium seed husk has not been sanitized prior to mixing with the alkaline solution. If the unmilled psyllium seed husk is sanitized by any method known in the art, such as steam sanitation, prior to the alkaline solubilization step, this disinfection step is not necessary. Disinfection refers to inactivating, destroying, eliminating, or inhibiting the growth of microorganisms. In one embodiment these microorganisms are disease-producing agents. Disinfection of the combined alkali soluble and alkali insoluble fractions may be conducted by any means known in the art. For example, pasteurization, irradiation, electron beam and pulsed light are all acceptable means of disinfecting the alkali soluble and alkali insoluble fraction mixture. In one embodiment, the mixture is pasteurized. Pasteurization entails heating the mixture to a moderate temperature for a period of time to disinfect, without changing, to any extent, the chemical composition of the mixture. Pasteurization may be carried out at a temperature of from about 90° C. to about 120° C. for a period of from about 30 seconds to about 120 seconds.

The alkali insoluble material is separated from the alkali soluble materials in Step 3 of the fractionation. This can be accomplished by any separation means known in the art that will not alter substantially the insoluble material, for example centrifugation. One skilled in the art will know how to alter the time and force of the centrifugation to adapt the separation to different centrifuge rotors, plant materials and alkaline solutions. Other methods to accomplish this separation are well known in the art and may be better suited for large-scale production of the gel-forming polysaccharide, such as settling, filtration, or expression. Optionally, the insoluble material can be further washed with the alkaline solution and re-separated in an effort to improve the yield of the alkaline soluble material.

In Step 4 of the instant process, the alkaline soluble materials are acidified to a pH of from about 4.5 to about 6.5, in one embodiment from about 5 to about 6, to yield an acid gel-forming material, i.e., a gel-forming polysaccharide. Suitable acids for acidification include, but are not limited to, acetic, hydrochloric, sulfuric, oxalic, trichloroacetic and trifluoroacetic acids. The duration and temperature of the acidification can vary. The acidification may suitably take place at ambient temperature for about 2 hours, though the time and temperature may vary.

Optionally, a second extraction may be appropriate at this stage of the fractionation process. Where desired, the acid soluble and acid gel-forming fractions may be separated, by any means known in the art, such as centrifugation, settling, straining and the like. Again an optional washing with water, buffer, or other suitable solvent may be employed to improve the efficiency of the separation. This second extraction may be employed to deliver a more purified gel-forming polysaccharide, but may also lead to degradation and loss of some of the gel-forming polysaccharide. It has been found that multiple extraction steps are not necessary to yield a suitable gel-forming polysaccharide with increased swell volume and a reduced in gelation rate.

Excess water is then removed from the acid gel-forming polysaccharide fraction in Step 5 of the fractionation process. Any method known in the art may be used to dewater the gel material. In one embodiment the gel material may be dewatered by desiccation with a solvent, such as ethanol, acetone, methanol or isopropyl alcohol. The addition of the solvent may occur with high shear mixing. The gel material is then separated from the solvent/water mixture by any method known in the art. For ease and simplicity of drying, the solids content of the gel material should be at least about 50%, in one embodiment the solids content is at least about 75%, in another embodiment the solids content of the gel material is about 80%.

The gel material may be dried in any manner known in the art, such as lyophilization, fluidized bed drying or vacuum tray drying. In one embodiment, fluidized bed drying of the gelatinous material is employed. The gel material is extruded to form small grain-like particles and placed into a fluidized bed dryer. The fluidized bed dryer may be equipped to provide a cyclonic airflow, which helps prevent the particles sticking together and allows the particles to fluidize. The extruded particles are suspended in the column of air until dried to at least about 85% solids content. During drying, the gel material should be maintained at a temperature of less than about 75° C. It is preferred that the solids content of the gel material is greater than about 20% prior to fluidized bed drying. If necessary, previously dried gel material may be added by mixing to the low solids content gel material, prior to fluidized bed drying, to increase the solids content to greater than about 20%. Not intending to be bound by theory, it is believed that the fluidized bed drying technique renders a gel-forming polysaccharide component wherein the individual particles retain a honeycomb shape. The honeycomb shape is useful to facilitate compression of the gel-forming polysaccharide powder, particularly by direct compression means, into a solid dosage form.

Methods of the Present Invention

The compositions of the present invention are useful for the treatment of gastrointestinal disorders. These formulations can be used alone or in combination with other active substances for the treatment of constipation and laxation and for normalizing bowel function. The compositions of the present invention may also be effective for providing more complete evacuation of the bowel and thereby rendering a detoxifying effect. In addition, the compositions are useful for reducing human serum cholesterol and controlling blood glucose levels in diabetics and may be used alone or in conjunction with other actives substances. Accordingly, the present invention relates to methods of providing a benefit selected from normalizing bowel function, inducing laxation, providing dietary fiber, reducing serum cholesterol levels, and combinations thereof, comprising administering a composition as described herein to a mammal in need of such benefit. Preferred mammals include humans, as well as companion animals such as domestic cats, dogs, horses, cows, and the like.

As used herein, the term "administer" with regard to a particular composition means to provide the composition to a mammal (including oneself) and/or to direct, instruct, or advise the use of the composition for any purpose (preferably, for a benefit described herein). Wherein the administration of one or more of the present compositions or kits is directed, instructed or advised, such direction may be that which instructs and/or informs the user that use of the composition may and/or will provide one or more of the benefits described herein. Non-limiting examples of such instruction or information are set forth herein as part of the description of the present kits.

Administration which is directed may comprise, for example, oral direction (e.g., through oral instruction from, for example, a physician, health professional, sales professional or organization, and/or radio or television media (i.e., advertisement) or written direction (e.g., through written direction from, for example, a physician or other health professional (e.g., scripts), sales professional or organization (e.g., through, for example, marketing brochures, pamphlets, or other instructive paraphernalia), written media (e.g., internet, electronic mail, or other computer-related media), and/or packaging associated with the composition (e.g., a label present on a package containing the composition). As used herein, "written" includes through words, pictures, symbols, and/or other visible descriptors. Such direction need not utilize the actual words used herein, but rather use of words, pictures, symbols, and the like conveying the same or similar meaning are contemplated within the scope of this invention.

Oral administration is preferred. As an example, a single administration of the present compositions may comprise from about 100 mg to about 5000 mg of the polysaccharide component, in one embodiment from about 1000 mg to about 1500 mg of the polysaccharide component.

Frequency of administration is not limited. However, the present compositions are typically administered on an infrequent or as-needed basis or may be administered in a more routine manner weekly, daily, or on a more or less frequent basis. For example, the composition may be administered with meals at least once daily, or alternatively at least two to three times daily. The compositions are often administered from about 1 to about 3 times per day.

It is understood that these descriptions are by way of example only, and that administration can be adjusted depending on various factors. The specific dosage of the component to be administered, as well as the duration of treatment, are interdependent. The dosage and treatment regimen will also depend upon such factors as the specific composition used, the treatment indication, the efficacy of the composition, the personal attributes of the mammal (such as, for example, weight, age, gender and medical condition of the mammal), compliance with the treatment regimen, and the like.

The present compositions are particularly suited for admixture with an aqueous liquid prior to administration. Indeed, the present inventors have developed the invention herein such that aqueous solutions or dispersions may be conveniently and effectively delivered to the consumer. As such, the present methods include admixture with an aqueous liquid, such as water or juice (for example, fruit or vegetable juice). Any aqueous liquid may be utilized, and will often be determined by preference of the consumer. Compositions comprising an aqueous liquid will typically comprise, for example, at least about 20% of such aqueous liquid, or from about 40% to about 99.9%, or from about 60% to about 98%, or from about 70% to about 96% of such aqueous liquid, all by weight of the composition.

EXAMPLES OF THE PRESENT INVENTION

The following are examples of the present components, compositions, and methods. The compositions are prepared utilizing conventional processes or, preferably, the processes described herein. The examples are provided to illustrate the invention and are not intended to limit the scope thereof in any manner.

Example 1

A polysaccharide component useful in the present invention is prepared as follows. Raw, unmilled psyllium seed husk (2 grams) is stirred with 0.2N sodium hydroxide (400 milliliters) containing sodium borohydride (400 milligrams) in a nitrogen atmosphere at ambient temperature for 90 minutes. The pH of the solution is from 10 to 11. The solution is passed through a pasteurizer at a temperature of 100° C. for a period of 50 seconds. Once pasteurized, the mixture is centrifuged for 20 minutes at 23,500×g. The supernatant is decanted from an insoluble fraction that settles out in the centrifuge bottle. The insoluble fraction is mixed with fresh sodium hydroxide/sodium borohydride solution (100 milliliters) and recentrifuged for 15 minutes to increase yield of the soluble fraction. The pH of the supernatant is adjusted to 5.5 by the addition of acetic acid at ambient temperature with stirring, forming a gel. The gel is desiccated with isopropanol added with high shear mixing. The isopropanol solution is then decanted from the gel. The solids content of the gel is 30%. The gel is passed through an extruder and extruded into individual particles. The extruded particles enter a fluidized bed dryer fitted with a cyclonic airflow screen, such as a Conidur screen. The air temperature is maintained at 80° C. The gel temperature remains below 70° C. throughout the drying process. The particles are dried to a powder, providing the resulting polysaccharide component at a yield of approximately 85%.

Example 2

A composition is prepared having a surrounding layer, containing indicated components at the indicated amounts:

| Component | Amount (wt %) |
| --- | --- |
| Polysaccharide Component | 85.0 |
| Stearic Acid | 15.0 |

The stearic acid is melted at a temperature of about 70° C. The polysaccharide component is suspended in a Wurster column at an inlet air temperature range of from about 55° C. to about 60° C. The molten stearic acid is sprayed to the surface of the polysaccharide component.

Example 3

A composition is prepared having a first surrounding layer and a second surrounding layer, containing indicated components at the indicated amounts:

| Component | Amount (wt %) |
| --- | --- |
| Polysaccharide Component | 85.0 |
| Stearic Acid | 10.0 |
| Gum Acacia | 5.0 |

The stearic acid is melted at a temperature of about 70° C. The polysaccharide component is suspended in a Wurster column at an inlet air temperature range of from about 55° C. to about 60° C. The molten stearic acid is sprayed to the surface of the polysaccharide component. The gum acacia is dissolved in water (about 5 grams per 50 milliliters water). In a fluid bed coater, top-down spray is used to deliver the gum acacia solution to the stearic acid-coated polysaccharide component.

Example 4

A composition is prepared having a first surrounding layer and a second surrounding layer, containing indicated components at the indicated amounts:

| Component | Amount (wt %) |
|---|---|
| Polysaccharide Component | 80.0 |
| Stearic Acid | 13.0 |
| Gum Acacia | 5.0 |
| TWEEN 80 | 2.0 |

The stearic acid is melted at a temperature of about 70° C. The polysaccharide component is suspended in a Wurster column at an inlet air temperature range of from about 55° C. to about 60° C. The molten stearic acid is sprayed to the surface of the polysaccharide component. The gum acacia and TWEEN 80 are dissolved in water (about 5 grams per 50 milliliters water). In a fluid bed coater, top-down spray is used to deliver the gum acacia/TWEEN 80 solution to the stearic acid-coated polysaccharide component.

Example 5

A composition is prepared having a surrounding layer, containing indicated components at the indicated amounts:

| Component | Amount (wt %) |
|---|---|
| Polysaccharide Component | 80.0 |
| Eudragit E30D (polymethacrylate) | 15.0 |
| Diethyl Phthalate | 5.0 |

The Eudragit E30D is dissolved in water. The diethyl phthalate is added to the resulting solution to provide a mixture. The mixture is suspending in 40° C. inlet air in a fluid bed coater. The mixture is then sprayed onto the polysaccharide component using top-down spray.

In each of Examples 2, 3, 4, and 5, the polysaccharide component is in accordance with the descriptions herein. As one example, the polysaccharide component comprises Fraction B as described in U.S. Pat. No. 6,287,609. As another example, the polysaccharide component comprises Fractions B and C as described in U.S. Pat. No. 6,287,609. As yet another example, the polysaccharide component has any, any combination, or all of the following components at the indicated levels:

| Component | Level present in polysaccharide component, by weight of the polysaccharide component |
|---|---|
| Xylose | From about 55% to about 70% |
| Arabinose | From about 15% to about 20% |
| Rhamnose | From 0% to about 5% |
| Mannose | From 0 to about 0.5% |
| Galactose | From about 1% to about 2% |
| Glucose | From 0% to about 0.5% |
| Uronic Acid | From about 0.5% to about 50% |

In each of Examples 2, 3, 4, and 5, agglomerates containing the polysaccharide component are formed. The agglomerates are optionally milled to a mean particle size distribution of about 200 microns. The agglomerates are dry blended with optional components, for example, starches, gums, flavorants, colorants, and sweeteners.

Example 6

Approximately 9.5 grams of a composition in accordance with any of Examples 2, 3, 4, or 5 is prepared, providing a single dose of the composition. The composition is dispersed in approximately 240 milliliters of water or orange juice. The composition is administered once daily to a human in need of normalized bowel function. A similar composition is administered twice daily to a human in need of reduced serum cholesterol levels.

What is claimed is:

1. A composition comprising a plurality of agglomerates comprising a polysaccharide component comprising xylose and arabinose, wherein the ratio of xylose to arabinose is at least about 3:1, by weight; wherein the composition further comprises:
   (i) optionally, a first surrounding layer which surrounds the agglomerates, wherein the first surrounding layer is a hydrophobic layer; and
   (ii) optionally, a second surrounding layer which surrounds the agglomerates, wherein the second surrounding layer is a hydrophilic layer;
wherein the composition comprises at least one of the first surrounding layer and the second surrounding layer, and wherein when the composition comprises the first surrounding layer and the second surrounding layer then the first surrounding layer is a preceding layer relative to the second surrounding layer.

2. The composition according to claim 1 wherein the agglomerates comprises from about 10% to about 90% of polysaccharide component, by weight of composition.

3. The composition according to claim 1 wherein the agglomerates comprises from about 20% to about 50% of polysaccharide component, by weight of composition.

4. The composition according to claim 1 wherein the agglomerates comprises from about 30% to about 70% of polysaccharide component, by weight of composition.

5. The composition according to claim 1 wherein the agglomerates each, independently, comprise the first surrounding layer, wherein the first surrounding layer exhibits a water vapor transmission rate of less than about 200 mg/m$^2$/24 hours.

6. The composition according to claim 5 wherein the first surrounding layer exhibits a water vapor transmission rate of less than about 100 mg/m$^2$/24 hours.

7. The composition according to claim 6 wherein the first surrounding layer comprises a component selected from the group consisting of fatty acids, fatty acid derivatives, polymers, and mixtures thereof.

8. The composition according to claim 1 wherein the agglomerates each, independently, comprise the second surrounding layer, wherein the second surrounding layer comprises a component selected from the group consisting of surfactants, gums, inorganic salts, and mixtures thereof.

9. The composition according to claim 8 wherein the agglomerates each, independently, comprise the first surrounding layer.

10. The composition according to claim 9 wherein the first surrounding layer exhibits a water vapor transmission rate of less than about 200 mg/m$^2$/24 hours.

11. The composition according to claim 10 wherein the first surrounding layer has a coating weight of from about 3 mg/cm$^2$ to about 25 mg/cm$^2$.

12. The composition according to claim 8 wherein the first surrounding layer comprises a component selected from the group consisting of fatty acids, fatty acid derivatives, polymers, and mixtures thereof.

13. The composition according to claim 8 wherein the mean particle size of the agglomerates is from about 100 microns to about 400 microns.

14. The composition according to claim 8 wherein the ratio of xylose to arabinose is from about 3:1 to about 6:1, by weight.

15. The composition according to claim 14 wherein the polysaccharide component further comprises a component selected from the group consisting of galactose, glucose, uronic acid, and mixtures thereof.

16. The composition according to claim 15 wherein the agglomerates each, independently, comprise a dispersing component, wherein the dispersing component is selected from the group consisting of binders, suspending agents, edible acids, and mixtures thereof.

17. The composition according to claim 16 wherein the dispersing component comprises maltodextrin.

18. The composition according to claim 17 wherein the agglomerates each, independently, comprise an edible acid.

19. The composition according to claim 18 wherein the edible acid is citric acid.

20. The composition according to claim 16 comprising a starch, wherein the agglomerates and at least a portion of the starch are physically distinct.

21. The composition according to claim 16 comprising a gum, wherein the agglomerates and at least a portion of the gum are physically distinct.

22. A method of providing a benefit selected from the group consisting of normalizing bowel function, inducing laxation, providing dietary fiber, reducing serum cholesterol levels, and combinations thereof, comprising orally administering a product comprising the composition according to claim 1 to a mammal in need of the benefit.

23. The method according to claim 22 comprising admixing the composition thereof with an aqueous liquid to form the product.

24. A composition comprising a plurality of polysaccharide particles, wherein the polysaccharide particles comprise a polysaccharide component comprising xylose and arabinose, wherein the ratio of the xylose to the arabinose is at least about 3:1, by weight, and wherein the polysaccharide particles have a mean particle size distribution of from about 0.001 microns to about 150 microns, wherein the polysaccharide particles each, independently, comprise:
  (i) optionally, a first surrounding layer which surrounds the particle, wherein the first surrounding layer is a hydrophobic layer; and
  (ii) optionally, a second surrounding layer which surrounds the particle, wherein the second surrounding layer is a hydrophilic layer;
wherein the polysaccharide particles each, independently, comprise at least one of the first surrounding layer and the second surrounding layer, and wherein when the particle comprises the first surrounding layer and the second surrounding layer then the first surrounding layer is a preceding layer relative to the second surrounding layer.

25. The composition according to claim 24 wherein the polysaccharide particles each, independently, comprise the first surrounding layer, wherein the first surrounding layer exhibits a water vapor transmission rate of less than about 200 mg/m$^2$/24 hours.

26. The composition according to claim 25 wherein the first surrounding layer exhibits a water vapor transmission rate of less than about 100 mg/m$^2$/24 hours.

27. The composition according to claim 26 wherein the first surrounding layer comprises a component selected from the group consisting of fatty acids, fatty acid derivatives, polymers, and mixtures thereof.

28. The composition according to claim 24 wherein the polysaccharide particles each, independently, comprise the second surrounding layer, wherein the second surrounding layer comprises a component selected from the group consisting of surfactants, gums, inorganic salts, and mixtures thereof.

29. The composition according to claim 28 wherein the polysaccharide particles each, independently, comprise the first surrounding layer.

30. The composition according to claim 29 wherein the first surrounding layer exhibits a water vapor transmission rate of less than about 200 mg/m$^2$/24 hours.

31. The composition according to claim 30 wherein the first surrounding layer has a coating weight of from about 3 mg/cm$^2$ to about 25 mg/cm$^2$.

32. The composition according to claim 28 wherein the first surrounding layer comprises a component selected from the group consisting of fatty acids, fatty acid derivatives, polymers, and mixtures thereof.

33. The composition according to claim 28 wherein the mean particle size of the polysaccharide particles is from about 0.001 microns to about 150 microns.

34. The composition according to claim 28 wherein the ratio of xylose to arabinose is from about 3:1 to about 6:1, by weight.

35. The composition according to claim 34 wherein the polysaccharide component further comprises a component selected from the group consisting of galactose, glucose, uronic acid, and mixtures thereof.

36. The composition according to claim 35 wherein the composition comprises a dispersing component, wherein the dispersing component is selected from the group consisting of binders, suspending agents, edible acids, and mixtures thereof.

37. The composition according to claim 36 wherein the dispersing component comprises maltodextrin.

38. The composition according to claim 37 wherein the dispersing component comprises an edible acid.

39. The composition according to claim 38 wherein the edible acid is citric acid.

40. The composition according to claim 36 wherein the dispersing component comprises a starch.

41. The composition according to claim 40 wherein the dispersing component comprises a gum.

42. The composition according to claim 36 comprising a plurality of agglomerates, wherein the agglomerates comprise at least a portion of the polysaccharide particles and at least a portion of the dispersing component.

43. A method of providing a benefit selected from the group consisting of normalizing bowel function, inducing laxation, providing dietary fiber, reducing serum cholesterol levels, and combinations thereof, comprising orally administering a product comprising the composition according to claim 24 to a mammal in need of the benefit.

44. The method according to claim 43 comprising admixing the composition thereof with an aqueous liquid to form the product.

* * * * *